United States Patent
Hua et al.

(10) Patent No.: US 12,044,475 B2
(45) Date of Patent: Jul. 23, 2024

(54) THERMAL PRETREATMENT METHOD AND EQUIPMENT FOR ORGANIC SOLID WASTE BASED ON FORCED HOT AIR CONVECTION

(71) Applicant: Tongji University, Shanghai (CN)

(72) Inventors: Yu Hua, Shanghai (CN); Xiaohu Dai, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 18/449,645

(22) Filed: Aug. 14, 2023

(65) Prior Publication Data
US 2024/0027134 A1    Jan. 25, 2024

(30) Foreign Application Priority Data
Aug. 18, 2022 (CN) .......................... 202210992212.7

(51) Int. Cl.
*F27B 17/00* (2006.01)
*B09B 3/40* (2022.01)
*B09B 3/60* (2022.01)
*C12M 1/00* (2006.01)
*F27D 11/02* (2006.01)

(52) U.S. Cl.
CPC ............ *F27B 17/0016* (2013.01); *B09B 3/40* (2022.01); *B09B 3/60* (2022.01); *C12M 45/09* (2013.01); *C12M 45/20* (2013.01); *C12Y 302/01004* (2013.01); *C12Y 302/01008* (2013.01); *F27D 11/02* (2013.01)

(58) Field of Classification Search
None
See application file for complete search history.

(56) References Cited

U.S. PATENT DOCUMENTS 3,802,089 A * 4/1974 Stephanoff .............. C02F 11/13
                                                         34/58
5,850,977 A * 12/1998 Csendes ................ B02C 19/005
                                                         241/24.31
(Continued)

FOREIGN PATENT DOCUMENTS

CN           1522805 A     8/2004
CN       205436435 U       8/2016
(Continued)

OTHER PUBLICATIONS

Li Ma et al., "Structural Properties and Composition of Paulownia:Effect of Acetic Acid and Sodium Sulfite Combined Pretreatment", Spectroscopy and Spectral Analysis, Feb. 2020, vol. 40, No. 2, pp. 523-528.
(Continued)

*Primary Examiner* — Thor S Campbell

(57) ABSTRACT

A thermal pretreatment method for organic solid waste based on forced hot air convection is performed as follows. Experimental materials are grouped into an experimental group and a control group. The experimental group is subjected to thermal pretreatment in a thermal pretreatment device, and then removed. The experimental group and the control group are subjected to enzymatic hydrolysis and physicochemical characterization, and the analysis results are compared. A thermal pretreatment device for organic solid waste based on forced hot air convection is also provided.

5 Claims, 3 Drawing Sheets

(56) References Cited

U.S. PATENT DOCUMENTS

| | | | | |
|---|---|---|---|---|
| 6,256,902 | B1* | 7/2001 | Flaherty | F26B 17/101 |
| | | | | 34/387 |
| 6,397,490 | B1* | 6/2002 | Inoki | F26B 17/103 |
| | | | | 34/168 |
| 7,954,740 | B2* | 6/2011 | Chen | B02C 19/066 |
| | | | | 241/62 |
| 7,967,226 | B2* | 6/2011 | Gocke | B02C 13/1814 |
| | | | | 241/119 |
| 8,105,400 | B2* | 1/2012 | Bergman | C10L 5/40 |
| | | | | 422/235 |
| 8,518,353 | B1* | 8/2013 | Neathery | B01D 53/508 |
| | | | | 423/244.01 |
| 9,091,481 | B2* | 7/2015 | Lankinen | F27D 17/004 |
| 10,036,592 | B2* | 7/2018 | Chen | F26B 3/04 |
| 10,553,460 | B2* | 2/2020 | Zuo | F26B 21/10 |
| 11,369,973 | B2* | 6/2022 | Vashkovskyi | B02C 13/18 |
| 11,660,605 | B2* | 5/2023 | Aumund | B02C 23/30 |
| | | | | 241/34 |
| 2009/0050134 | A1* | 2/2009 | Friend | C13K 1/02 |
| | | | | 127/29 |
| 2009/0053770 | A1* | 2/2009 | Hennessey | D21C 11/0007 |
| | | | | 435/163 |
| 2010/0162619 | A1* | 7/2010 | Peus | C10L 9/083 |
| | | | | 44/605 |
| 2010/0242351 | A1* | 9/2010 | Causer | F23G 5/04 |
| | | | | 110/224 |
| 2012/0266485 | A1* | 10/2012 | Abraham | C10B 49/02 |
| | | | | 34/61 |
| 2017/0261260 | A1* | 9/2017 | Chen | F26B 3/04 |

FOREIGN PATENT DOCUMENTS

| | | | | |
|---|---|---|---|---|
| CN | 207101545 | U | * | 3/2018 |
| CN | 109055437 | A | | 12/2018 |
| CN | 208636731 | U | | 3/2019 |
| CN | 111437916 | A | | 7/2020 |
| CN | 211179772 | U | | 8/2020 |
| CN | 112747324 | A | | 5/2021 |
| CN | 213107668 | U | * | 5/2021 |
| CN | 214844310 | U | * | 11/2021 |
| CN | 215065587 | U | | 12/2021 |
| CN | 114656986 | A | | 6/2022 |
| CN | 114716270 | A | | 7/2022 |
| CN | 217737211 | U | * | 11/2022 |
| WO | 2015136490 | A1 | | 9/2015 |
| WO | WO-2015136490 | A1 | * | 9/2015 ............... B01J 8/10 |
| WO | WO-2019092314 | A1 | * | 5/2019 |

OTHER PUBLICATIONS

Jiading Xiong et al., "Effects of Thermo-Hydrogen Peroxide Pretreatment on Enzymatic Hydrolysis of Peanut Straw", Acta Energiae Solaris Sinica, Sep. 2018, vol. 39, No. 9, pp. 2569-2575.

Qian Du et al., "Analysis of ingredient and calorific value difference of different pretreatment biomass", Chemical Engineer, 2015, No. 3, pp. 8-11.

* cited by examiner

THERMAL PRETREATMENT METHOD AND EQUIPMENT FOR ORGANIC SOLID WASTE BASED ON FORCED HOT AIR CONVECTION

CROSS-REFERENCE TO RELATED APPLICATIONS

This application claims the benefit of priority from Chinese Patent Application No. 202210992212.7, filed on Aug. 18, 2022. The content of the aforementioned application, including any intervening amendments thereto, is incorporated herein by reference in its entirety.

TECHNICAL FIELD

The present disclosure relates to pretreatment of organic solid waste, and more particularly to a thermal pretreatment method and equipment for organic solid waste based on forced hot air convection.

BACKGROUND

Biochemical conversion is one of the main ways to convert straw into biomass energy, in which cellulose and hemicellulose are first degraded into small-molecule carbohydrate under the action of microorganisms and enzymes secreted thereby, which are then fermented to produce energy sources such as ethanol, methane, and hydrogen. The production of functional substances from sugar has been widely applied in the field of food chemistry. Regarding the anaerobic fermentation, a great advancement has been accomplished not only in terms of theorical research, but also in terms of enhanced transformation, especially in the application of interspecies electron transfer between microorganisms and the development of bioreactors. However, direct use of raw straw to produce sugar as a bio-platform molecule in the front-end process of biochemical conversion is less efficient, which is considered as an important challenge limiting the efficient conversion of straw into bio-products/bio-fuels. Natural resistance to enzymatic and microbial deconstruction is generated by the crosslinked supramolecular structure in biomass, which is collectively known as the biomass recalcitrance. Therefore, the pretreatment of raw straw prior to biochemical treatment is essential.

In order to ensure the efficiency of the subsequent biochemical treatment, the pretreatment process should overcome the biomass recalcitrance while minimizing the loss of nutrients, thus enhancing the contact between the enzyme and the active site of the degradable substrate. The pretreatment can be performed by a physical, chemical, or biological approach, or a combination thereof in practice. However, these pretreatment methods have certain limitations, such as high reagent costs, large equipment investment, high mechanical energy consumption, secondary pollution and high process control requirements. By comparison, thermal pretreatment has become one of the most commonly used pretreatment methods due to its convenient operation, simple process control, and no secondary pollution caused by reagents. Additionally, the thermal pretreatment can be further subdivided into simple thermal pretreatment, steam explosion pretreatment, and hydrothermal pretreatment.

The thermal pretreatment is generally performed at 50° C.-220° C., and the sugar yield of straw can be increased by 15% to 50% after pretreatment, which is mainly due to the destabilization of lignocellulose cross-linking state. Compositionally, the thermal pretreatment can reduce the absolute content of hemicellulose and increase the relative content of cellulose, which is more conducive to the cellulase-mediated catalysis. Microbially-available hemicellulose forms a coating on the cellulose surface, and is linked to lignin by hydrogen bonding, which also means that a major bottleneck in the thermal pretreatment is how to reduce the loss of biodegradable hemicellulose. Surfactants are usually added to improve the removal of hydrophobic substances by reducing the surface sliding between two phases, thus enhancing the surface hydrophilicity of the straw to facilitate hydrolysis and mass transfer processes. Therefore, it is urgently needed to develop a novel thermal pretreatment method and equipment for organic solid waste based on forced hot air convection to solve the above problems.

SUMMARY

An object of this application is to provide a thermal pretreatment method and equipment for organic solid waste based on forced hot air convection to overcome the above problems in the prior art.

Technical solutions of this application will be specifically described as follows.

This application provides a thermal pretreatment method for organic solid waste (OSW) based on forced hot air convection, comprising:
(a) grouping experimental materials into an experimental group and a control group;
(b) placing the experimental group into an OSW thermal pretreatment device based on forced hot air convection for thermal pretreatment;
(c) removing the experimental group from the OSW thermal pretreatment device; and
(d) subjecting the experimental group and the control group to enzymatic hydrolysis and physicochemical analysis in sequence to obtain analysis results of the experimental group and analysis results of the control group; and comparing the analysis results of the experimental group with the analysis results of the control group.

In an embodiment, in the step (a), a particle size of the experimental material is less than 1 mm.

In an embodiment, in the step (c), after removing the experimental group from the OSW thermal pretreatment device, cooling the experimental group to room temperature, and storing the experimental group in a dry environment.

In an embodiment, in the step (d), the physicochemical analysis comprises functional group identification based on Fourier Transform Infrared (FTIR) spectroscopy, surface chemical composition determination based on X-ray photoelectron spectroscopy, surface roughness characterization based on atomic force microscopy, crystallinity determination based on X-ray diffraction, BET adsorption properties, vacuum density and contact angle analysis.

This application also provides a thermal pretreatment device for organic solid waste (OSW) based on forced hot air convection, comprising: a box;
wherein a top surface of the box is rotatably connected with a top cover; the box is hollow, and a reaction chamber is fixedly provided in the box; the experimental group is arranged in the reaction chamber; a bottom surface of the reaction chamber is communicated with an inside of the box; a top of the reaction chamber is detachably connected with a moveable cover; a heat dissipating mechanism is provided on the top cover, the heat dissipating mechanism comprises an electric heating wire fixedly provided in the top cover; a top of the electric heating wire is provided with a heat dissipating portion; and a plurality of locking mechanisms are provided evenly spaced apart between the top cover and an inner wall of the box.

In an embodiment, a side wall of the box is hollow; each of the plurality of locking mechanism comprises a first connecting plate fixedly connected to the inner wall of the box; the first connecting plate is hollow, and is connected to the side wall of the box; a second connecting plate is fixedly connected to a top surface of the first connecting plate; a first cavity is provided in the second connecting plate; a sliding groove is provided on a top surface of the second connecting plate, and is communicated with the first cavity; a slider is slidably connected with the sliding groove; an inner wall of the top cover is provided with a groove; the slider is configured to fit the groove; a transmission part is provided in the side wall of the box, and is in transmission connection with the slider.

In an embodiment, the transmission part comprises a first motor fixedly connected to the inner wall of the box; an output shaft of the first motor is fixedly connected to a connecting roller; the connecting roller is fixedly connected to a first end of a connecting rope; a second other end of the connecting rope passes through the first connecting plate, the first cavity and the sliding groove in turn, and is fixedly connected to the slider; a spring is fixedly connected between the slider and a side wall of the sliding groove; the connecting rope is arranged at a bottom of the spring.

In an embodiment, the sliding groove is provided with a first fixed pulley near a bottom of the first cavity; a second fixed pulley is fixedly provided in the first connecting plate; the connecting rope is arranged on a surface of the first fixed pulley and the second fixed pulley.

In an embodiment, the heat dissipating portion comprises a second motor fixedly connected to the inner wall of the top cover; an output shaft of the second motor is fixedly connected to a fan; and the fan is provided on the top of the electric heating wire.

In an embodiment, a second cavity is provided in the top cover; a controller is provided in the second cavity; a side of the top cover is provided with a temperature adjustment knob; the inner wall of the box is fixedly connected with a temperature sensor; the controller is electrically connected to the first motor, the second motor, the temperature adjustment knob, the temperature sensor and the electric heating wire.

This application has the following technical effects.

Two groups of the same experimental materials are set to facilitate the comparison of experimental data.

The experimental group is exposed to forced hot air convection in the thermal pretreatment device to achieve the surface coking. thereby effectively relieving the loss of internal organic substances while rendering the internal structure loose.

The pretreatment process of the present disclosure is conducive to the subsequent utilization of raw materials, such as enzymatic hydrolysis, saccharification or other biological transformation, allowing for enhanced utilization efficiency.

DESCRIPTION OF THE DRAWINGS

In order to illustrate the technical solutions of the embodiments of the present disclosure or the prior art more clearly, the drawings needed in the embodiments will be briefly described below. Obviously, the following drawings only illustrate some embodiments of the present disclosure and therefore should not be considered as limiting the scope of the disclosure. For those skilled in the art, other related drawings can be obtained according to these drawings without making any creative effort.

Figure 1:
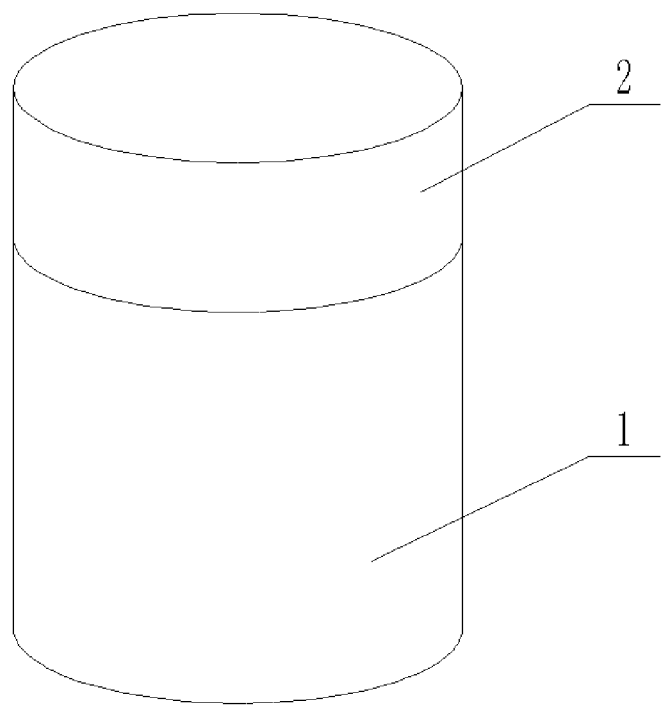
FIG. 1 schematically shows an external structural of a thermal pretreatment equipment according to an embodiment of this application.

In the drawings: 1. box; 2. top cover; 3. reaction chamber; 4. movable cover; 5. electric heating wire; 6. first connecting plate; 7. second connecting plate; 8. first cavity; 9. sliding groove; 10. slider; 11. groove; 12. first motor; 13. connecting roller; 14. connecting rope; 15. spring; 16. first fixed pulley; 17. second fixed pulley; 18. second motor; 19. fan; 20. second cavity; 21. controller; 22. temperature adjustment knob; 23. temperature sensor; 24. first ring groove; 25. sealing gasket; 26. second ring groove; 27. separator; 28. bearing; 29. ring separator; 30. connecting rod; and 31. first arc-shaped face.

DETAILED DESCRIPTION OF EMBODIMENTS

The technical solutions of the present disclosure will be fully illustrated below with reference to the drawings and the embodiments of the disclosure. Obviously, described below are merely some embodiments of the present disclosure, and not all embodiments. All other embodiments obtained by those skilled in the art without making any creative effort shall fall within the scope of this disclosure.

In order to illustrate the objects, technical solutions and advantages of this application more clearly, this application will be clearly and completely described below with reference to the drawings and embodiments.

Figure 2:
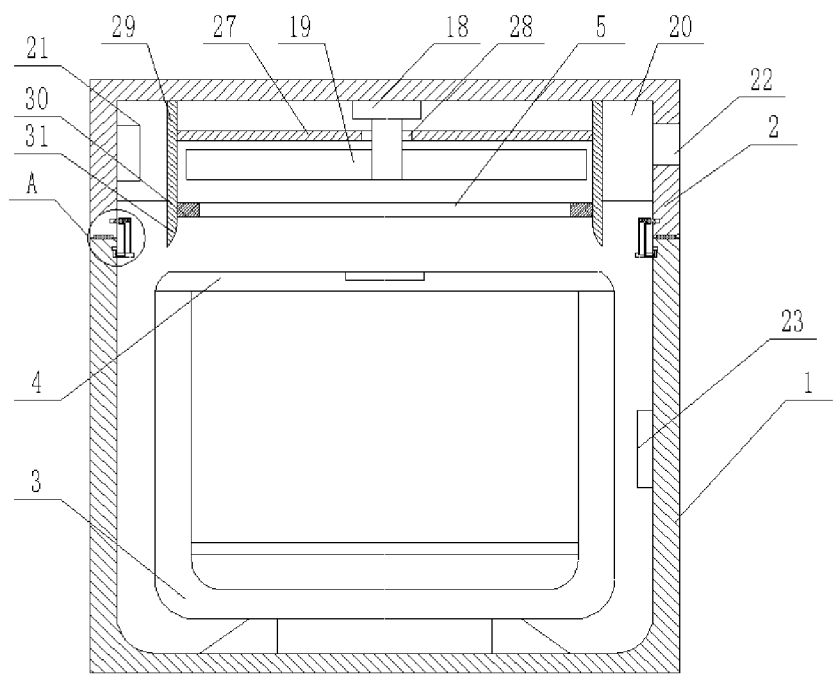
FIG. 2 schematically shows an internal structural of the thermal pretreatment equipment according to an embodiment of this application.
Figure 3:
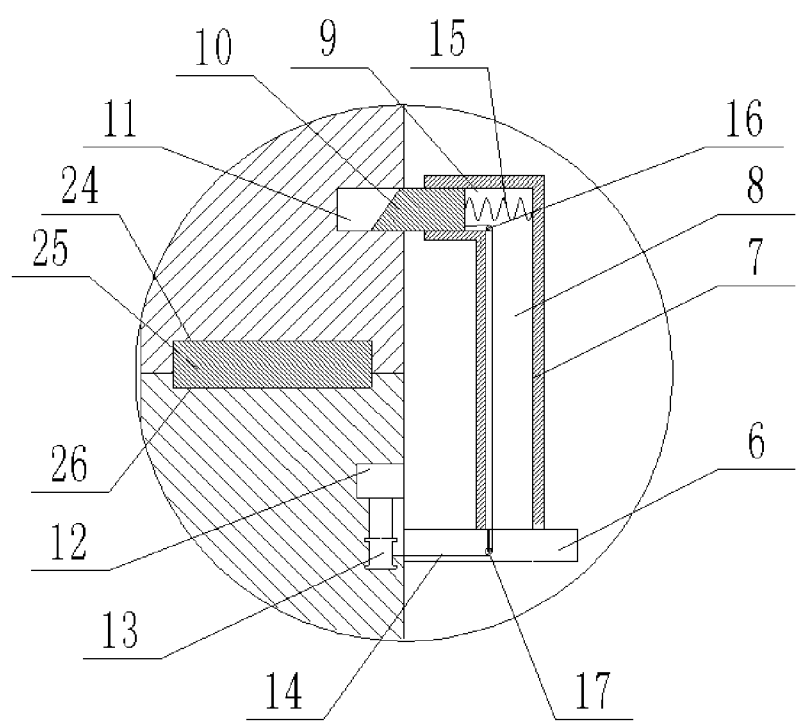
FIG. 3 is a partial enlarged view of part "A" of FIG. 2.

Referring to FIGS. 1-3, the present disclosure provides a novel thermal pretreatment method for organic solid waste based on forced hot air convection, including the following steps.

(a) Experimental materials are grouped into an experimental group and a control group.

(b) The experimental group was put into the organic solid waste thermal pretreatment device based on forced hot air convection for thermal pretreatment.

(c) The experimental group was removed from the thermal pretreatment device.

(d) The experimental group and the control group were subjected to enzymatic hydrolysis and physicochemical analysis in sequence, and the results were compared and analyzed.

Two groups of the same experimental materials are set to facilitate the comparison of experimental data. The experimental group is exposed to forced hot air convection in the thermal pretreatment device to achieve the surface coking (modifying), thereby effectively relieving the loss of internal organic substances while rendering the internal structure loose. The pretreatment process of the present disclosure is conducive to the subsequent utilization of raw materials, such as enzymatic hydrolysis, saccharification or other biological transformation, allowing for enhanced utilization efficiency.

In an embodiment, in the step (a), a particle size of the experimental material is less than 1 mm.

In this embodiment, the experimental materials were selected as mature and dry corn straw (CS) and rice straw (RS) after harvesting, and only the intact straw segments were retained, ground into powder and sieved to a particle size of less than 1 mm as experimental materials.

In an embodiment, in the step (c), the experimental groups (i.e., corn straw (CS) and rice straw (RS)) were removed and cooled to room temperature, the treated experimental groups were kept in a dry environment and the untreated samples of corn straw (CS) and rice straw (RS) were kept as control.

In an embodiment, in the step (d), the physicochemical analysis includes functional group identification based on Fourier Transform Infrared (FTTR) spectroscopy, surface chemical composition determination based on X-ray photoelectron spectroscopy, surface roughness characterization based on atomic force microscopy, crystallinity determination based on X-ray diffraction, BET adsorption properties, vacuum density and contact angle analysis.

The experimental groups of corn straw (CS) and rice straw (RS) pretreated by hot air forced convection and untreated corn straw (CS) and rice straw (RS) were subjected to enzymatic hydrolysis tests in 25 mL conical flasks with three replications for each group. An equal amount of 5% (w/v) dry matter was added to each bottle with 50 mmolL$^{-1}$ citrate buffer (pH 4.8). Sodium azide (0.02%, 100 μL) was added to prevent microbial growth. Cellulase and xylanase loads were maintained at 30 FPU (g-glucan)$^{-1}$ and 150 U (g-glucan)$^{-1}$, respectively. The enzymatic digestion was carried out at 50° C. for 72 h at 150 rpm. The concentration of sugars after enzymatic digestion was determined by ion chromatography equipped with a DionexCarbopac™ PA20 column and an electrochemical detector. The mobile phases were A-H$_2$O, B-250 mmolL$^{-1}$ NaOH, and C-50 mmolL$^{-1}$ NaOH&500 mmolL$^{-1}$ NaOAc at a flow rate of 0.3 mL min$^{-1}$. The total saccharification rate and cellulose conversion rate were calculated as follows.

$$\text{Toral saccharification rate} = \frac{RS \times 0.9}{HOLO} \times 100\% \quad (1)$$

$$\text{Cellulose conversion rate} = \frac{GLU \times 0.9}{CEL} \times 100\% \quad (2)$$

where RS is the reducing sugar content produced, g.
HOLO is the total cellulose content of biomass, g.
GLU is the glucose content generated, g.
CEL is the cellulose content of the biomass, g.

Four monosaccharides, glucose, xylose, galactose and arabinose, were detected in the supernatant. Regardless of the substrate, glucose was the major component in the enzymatic supernatant (>90%). The total saccharification rate and cellulose conversion rate increased after hot air forced convection pretreatment. The total saccharification rate of CS increased from 31.31±1.06% to 44.77±1.23%, and the cellulose conversion rate increased from 44.10±1.85% to 67.44±2.37%. Under this enzymatic digestion condition, the enzymatic digestion effect of untreated RS had reached the effect of pretreated CS. Hot air forced convection pretreatment did not significantly improve the enzymatic degradation of RS, the total saccharification rate only increased from 68.93±3.14% to 70.44±2.54%, and the cellulose conversion rate increased from 87.93±4.65% to 90.77±4.53%.

Fourier transform infrared (FTIR) spectroscopy for functional groups: 1 to 2 mg dried powder samples were mixed with 200 mg of spectrographic grade KBr and pressed into tablets of about 10 mm diameter and 1 mm thickness. The IR spectra were obtained from 4000 cm$^{-1}$ to 400 cm$^{-1}$ with a resolution of 4 cm$^{-1}$. The measured IR spectra were standardized using the max-min method.

Determination of surface chemical composition by X-ray photoelectron spectroscopy (XPS): the surface chemical composition of the samples was characterized by XPS using a spectrometer (K-Alpha, Thermo Fisher Scientific, USA) under an Al Kα X-ray excitation source (hv=1486.6 eV). The beam spot size was 250 μm, the vacuum of the analysis chamber was better than 5.0×10$^{-7}$ mBar. The operating voltage was 12 kV, and the filament current was 6 mA. The measured spectra were recorded in 1.0 eV steps and 200 eV through-energy, whereas the high-resolution spectra were recorded in 0.1 eV steps and 50 eV through-energy. The chemical composition was calculated from the photoelectron peak area and the chemical bonding composition was obtained from the respective spectrum deconvolution (Thermo Scientific TMA vantage). The $C_{1s}$ peak at 284.8 eV was used as a reference for charge correction.

Characterization of surface roughness factor by atomic force microscopy (AFM): The changes in surface morphology and roughness of the samples before and after AF pretreatment were observed using AFM. All experiments were carried out using the same AFM probe under the same environmental conditions (temperature of 25° C. and relative humidity of 25%). The images were analyzed using a Bruker Nanoscope V Multimode 8 scanning probe microscope. The root-mean-square roughness (Rq) of the height deviation was taken from the averaged image data plane, and the mean roughness (Ra) was the arithmetic mean of the absolute values of the surface height deviation measured from the averaged plane.

X-ray diffraction (XRD) calculations of crystallization were performed using a sealed-tube Cu Kα excitation source, and CS and RS samples before and after pretreatment were analyzed by X-ray diffraction. Scans were performed in the range of 2θ=5° to 90° at a speed of 2° min$^{-1}$. The peaks were analyzed by the peak inverse fold accumulation method and the peaks were fitted with MDI Jade 6.0 to calculate the degree of crystallinity.

BET adsorption properties, vacuum density and contact angle analysis. The BET adsorption properties of the samples were determined using N$_2$ as adsorbent and surface area and porosity analyzer. Vacuum density was measured with an AccuPyc 1330 hydrometer. Surface wettability or hydrophilicity was characterized by contact angle, which was further measured in images using ImageJ software.

A thermal pretreatment device for organic solid waste based on forced hot air convection, including a box 1. Atop surface of the box 1 is rotatably connected with a top cover 2. The box 1 is hollow and a reaction chamber 3 is fixedly provided in the box 1. The experimental group is arranged in the reaction chamber 3. A bottom surface of the reaction chamber 3 is communicated with an inside of the box 1. A moveable cover 4 is detachably attached to a top of the box 1. A heat dissipating mechanism is provided on the top cover 2, the heat dissipating mechanism includes an electric heating wire fixedly provided to the top cover 2. Atop of the electric heating wire 5 is provided with a heat dissipating portion. A plurality of locking mechanisms are provided evenly spaced apart between the top cover 2 and an inner wall of the box 1.

The top cover 2 is opened, and then the movable cover 4 is removed. The experimental group of corn straw (CS) and rice straw (RS) are put into the reaction chamber 3, and the movable cover 4 is closed, and then the top cover 2 is closed. The top cover 2 is locked by means of the locking mechanism to prevent the heat from overflowing out during the reaction process. The electric heating wire 5 is activated. The heat dissipation section blows the heat from the electric heating wire 5 along an inner wall of the box 1 to a bottom of the reaction chamber 3, causes the heat to enter into the reaction chamber 3 and heat the experimental group of corn straw (CS) and rice straw (RS) therein, so as to cause high-speed circulating heat flow to be formed in the interior of the box 1. The experimental group of corn straw (CS) and rice straw (RS) to be baked at high temperatures in a confined space.

In an embodiment, a side wall of the box 1 is hollow. Each of the plurality of locking mechanism includes a first connecting plate 6 fixedly connected to the inner wall of the box 1. The first connecting plate 6 is hollow inside and is connected to the side wall of the box 1. A second connecting plate 7 is fixedly connected to a top surface of the first connecting plate 6. A first cavity 8 is provided in the second connecting plate 7. A sliding groove 9 is provided on a top surface of the second connecting plate 7, and is connected to the first cavity 8. A slider 10 is slidingly connected inside the sliding groove 9. A groove 11 is provided in the inner wall of the top cover 2. The slider 10 is fitted to the groove 11. A transmission part is provided in the side wall of the box 1 and is in transmission connection with the slider 10.

When it is necessary to snap the top cover 2 together, the slider 10 is made to slide into the sliding groove 9 by means of a drive portion. After a bottom surface of the top cover 2 has been fitted to a top surface of the box 1, the drive portion is loosened, so that the slider 10 slides along the sliding groove 9 and enters into the groove 11, and locks the top cover 2.

In an embodiment, the transmission part includes a first motor 12 fixedly connected to the inner wall of the box 1. A connecting roller 13 is fixedly connected to an output shaft. A first end of a connecting rope 14 is fixedly connected to the connecting roller 13. A second end of the connecting rope 14 passes in turn through the first connecting plate 6, the first cavity 8 and the sliding groove 9, and is fixedly connected to the slider 10. A spring 15 is fixedly connected between the slider 10 and a side wall of the sliding groove 9. The connecting rope 14 is arranged at a bottom of the spring 15.

When the slider 10 is required to slide into the groove 9, the first motor 12 is started. The first motor 12 drives the connecting roller 13 to rotate. The connecting roller 13 winds the connecting rope 14 around the connecting roller 13, so that the connecting rope 14 is tightened. The connecting rope 14 pulls the slider 10 to slide toward the groove 9. At the same time the spring 15 is compressed. When the slider 10 is required to slide into the first recess 11, the first motor 12 rotate in the reverse direction, driving the connecting roller 13 to rotate in the reverse direction. The connecting roller 13 reduces the number of winding laps of connecting rope 14 in connecting roller 13. Meanwhile the spring 15 pushes the slider 10 to slide toward a side close to the groove 11, and makes the slider 10 enter into the groove 11.

In an embodiment, the sliding groove 9 is provided with a first fixed pulley 16 near a bottom of the first cavity 8. A second fixed pulley 17 is fixedly provided in the first connecting plate 6. The connecting rope 14 is arranged on a surface of the first fixed pulley 16 and the second fixed pulley 17.

By providing the first fixed wheel 16 and the second fixed wheel 17, the connecting rope 14 is prevented from being cut at the connection between the first cavity 8 and the sliding groove 9 and between the first cavity 8 and the first connecting plate 6. At the same time, the connecting rope 14 is made of a high-temperature resistant material.

A bottom surface of the top cover 2 is circumferentially provided with a first ring groove 24. A sealing gasket 25 is embedded in the first ring groove 24. A second ring groove 26 is circumferentially provided on a top surface of the box 1. A bottom portion of the sealing gasket 25 is arranged in the second ring groove 26.

In an embodiment, the heat dissipating portion includes a second motor 18 fixedly connected to the inner wall of the top cover 2. An output shaft of the second motor 18 is fixedly connected to a fan 19; and the fan 19 is provided on the top of the electric heating wire 5.

The fan 19 is configured to blow the heat from the electric heating wire 5 downwards. A separator 27 is fixedly connected between the fan 19 and the second motor 18. The separator 27 is rotationally connected to the output shaft of the second motor 18 via a bearing 28.

The inner wall of the top cover 2 is fixedly connected to a ring separator 29. A second cavity 20 is formed between the ring separator 29 and an inner wall of the top cover 2. The ring separator 29 is fixedly connected to a side of the separator 27 far away from the bearing 28. The ring separator 29 is fixedly connected to a connecting rod 30 on a side close to the separator 27. The connecting rod 30 is arranged at a bottom of the separator 27, and is fixedly connected to the electric heating wire 5.

A bottom surface of the ring separator 29 is provided with a first arc-shaped surface 31, and the first arc-shaped surface 31 is configured to changing the direction of heat conduction.

In an embodiment, a second cavity 20 is provided in the top cover 2. A controller 21 is provided in the second cavity 20. A side of the top cover is provided with a temperature adjustment knob 22. The inner wall of the box 1 is fixedly connected with a temperature sensor 23. The controller 21 is electrically connected to the first motor 12, the second motor 18, the temperature adjustment knob 22, the temperature sensor 23 and the electric heating wire 5.

In the description of the present disclosure, it is to be understood that orientation or positional relationships indicated by the terms "longitudinal", "lateral", "up", "down", "front", "back", "left", "right", "vertical", "horizontal", "top", "bottom", "inside", "outside", etc., are based on the drawings of the disclosure, and are only for the purpose of facilitating the description of the present disclosure, rather than indicating or implying that the device or element referred to must be constructed and operated in a particular orientation. Therefore, these terms should not be construed as limiting the disclosure.

Described above are only several preferred embodiments of the present disclosure, which should not be construed as a limitation on the scope of the disclosure. It should be pointed out that for those skilled in the art, several variations and improvements can be made without departing from the spirit of the present disclosure, all of which shall fall within the protection scope of the present disclosure defined by the appended claims.

What is claimed is:

1. A thermal pretreatment method for organic solid waste (OSW) based on forced hot air convection, comprising:
   (a) grouping experimental materials into an experimental group and a control group;
   (b) placing the experimental group into an OSW thermal pretreatment device based on forced hot air convection for thermal pretreatment;

(c) removing the experimental group from the OSW thermal pretreatment device; and (d) subjecting the experimental group and the control group to enzymatic hydrolysis and physicochemical analysis in sequence to obtain analysis results of the experimental group and analysis results of the control group; and comparing the analysis results of the experimental group with the analysis results of the control group;

wherein the OSW thermal pretreatment device comprises a box; a top surface of the box is rotatably connected with a top cover; the box is hollow, and a reaction chamber is fixedly provided in the box; the reaction chamber is configured to accommodate the experimental group; a bottom surface of the reaction chamber is communicated with an inside of the box; a top of the reaction chamber is detachably connected with a moveable cover; a heat dissipating mechanism is provided on the top cover; the heat dissipating mechanism comprises an electric heating wire fixedly provided in the top cover; a top of the electric heating wire is provided with a heat dissipating portion; and a plurality of locking mechanisms are provided evenly spaced apart between the top cover and an inner wall of the box;

a side wall of the box is hollow; each of the plurality of locking mechanisms comprises a first connecting plate fixedly connected to the inner wall of the box; the first connecting plate is hollow, and is connected to the side wall of the box; a second connecting plate is fixedly connected to a top surface of the first connecting plate; a first cavity is provided in the second connecting plate; a sliding groove is provided on a top surface of the second connecting plate, and is communicated with the first cavity; a slider is slidably connected with the sliding groove; an inner wall of the top cover is provided with a groove; the slider is configured to fit the groove; a transmission part is provided in the side wall of the box, and is in transmission connection with the slider;

the transmission part comprises a first motor fixedly connected to the inner wall of the box; an output shaft of the first motor is fixedly connected to a connecting roller; the connecting roller is fixedly connected to a first end of a connecting rope; a second other end of the connecting rope passes through the first connecting plate, the first cavity and the sliding groove in turn, and is fixedly connected to the slider; a spring is fixedly connected between the slider and a side wall of the sliding groove; and the connecting rope is arranged at a bottom of the spring;

the heat dissipating portion comprises a second motor fixedly connected to the inner wall of the top cover; an output shaft of the second motor is fixedly connected to a fan; and the fan is provided on the top of the electric heating wire; and a second cavity is provided in the top cover; a controller is provided in the second cavity; a side of the top cover is provided with a temperature adjustment knob; the inner wall of the box is fixedly connected with a temperature sensor; the controller is electrically connected to the first motor, the second motor, the temperature adjustment knob, the temperature sensor and the electric heating wire.

2. The thermal pretreatment method of claim 1, wherein in the step (a), a particle size of the experimental materials is less than 1 mm.

3. The thermal pretreatment method of claim 1, wherein the step (c) further comprises:

after removing the experimental group from the OSW thermal pretreatment device, cooling the experimental group to room temperature, and storing the experimental group in a dry environment.

4. The thermal pretreatment method of claim 1, wherein in the step (d), the physicochemical analysis comprises functional group identification based on Fourier Transform Infrared (FTIR) spectroscopy, surface chemical composition determination based on X-ray photoelectron spectroscopy, surface roughness characterization based on atomic force microscopy, crystallinity determination based on X-ray diffraction, BET adsorption properties, vacuum density and contact angle analysis.

5. The thermal pretreatment method of claim 1, wherein a portion of a bottom of the sliding groove near the first cavity is provided with a first fixed pulley; a second fixed pulley is fixedly provided in the first connecting plate; and the connecting rope is arranged on a surface of the first fixed pulley and a surface of the second fixed pulley.

* * * * *